US010107803B2

(12) United States Patent
Astier et al.

(10) Patent No.: US 10,107,803 B2
(45) Date of Patent: Oct. 23, 2018

(54) NANO-PILLAR-BASED BIOSENSING DEVICE

(71) Applicant: International Business Machines Corporation, Armonk, NY (US)

(72) Inventors: Yann Astier, Livermore, CA (US); Huan Hu, Yorktown Heights, NY (US); Ning Li, White Plains, NY (US); Devendra K. Sadana, Pleasantville, NY (US); Joshua T. Smith, Croton on Hudson, NY (US); William T. Spratt, Osssing, NY (US)

(73) Assignee: International Business Machines Corporation, Armonk, NY (US)

( * ) Notice: Subject to any disclaimer, the term of this patent is extended or adjusted under 35 U.S.C. 154(b) by 105 days.

(21) Appl. No.: 15/244,484

(22) Filed: Aug. 23, 2016

(65) Prior Publication Data
US 2017/0176424 A1   Jun. 22, 2017

Related U.S. Application Data

(62) Division of application No. 14/972,996, filed on Dec. 17, 2015, now Pat. No. 9,559,240.

(51) Int. Cl.
*B01L 3/00* (2006.01)
*G01N 15/14* (2006.01)
*G01N 21/64* (2006.01)
*G01N 33/543* (2006.01)
*G01N 15/00* (2006.01)

(52) U.S. Cl.
CPC .. *G01N 33/54306* (2013.01); *B01L 3/502761* (2013.01); *G01N 15/1436* (2013.01); *G01N 15/1484* (2013.01); *G01N 21/6428* (2013.01); *G01N 33/54373* (2013.01); *B01L 2200/0652* (2013.01); *B01L 2200/10* (2013.01); *B01L 2300/0627* (2013.01); *G01N 2015/0065* (2013.01); *G01N 2201/062* (2013.01)

(58) Field of Classification Search
CPC ......... B01L 2200/0652; B01L 2200/10; B01L 2300/0627; B01L 2300/12; B01L 3/502761; B01L 3/502715; G01N 15/1436; G01N 15/1484; G01N 2015/0065; G01N 21/6428; G01N 2201/062; G01N 33/54306; G01N 33/54373; H01L 31/125; H01L 31/18; H01L 31/02164; H01L 31/173; H01L 33/20; H01L 33/58
USPC ... 436/63, 86, 164, 165, 172, 174, 177, 180; 422/82.05, 82.08, 501, 502, 503, 507, 422/527; 435/287.1, 288.3, 288.7
See application file for complete search history.

(56) References Cited

U.S. PATENT DOCUMENTS

| 8,022,390 | B1 | 9/2011 | Kim | |
| 9,559,240 | B1 * | 1/2017 | Astier | H01L 31/125 |
| 9,719,926 | B2 * | 8/2017 | Astier | G01N 21/6428 |
| 9,812,605 | B2 * | 11/2017 | Astier | H01L 31/173 |
| 2006/0110839 | A1 | 5/2006 | Dawson | |

(Continued)

*Primary Examiner* — Maureen Wallenhorst
(74) *Attorney, Agent, or Firm* — Louis Percello

(57) ABSTRACT

In one example, a device includes a trench formed in a substrate. The trench includes a first end and a second end that are non-collinear. A first plurality of semiconductor pillars is positioned near the first end of the trench and includes integrated light sources. A second plurality of semiconductor pillars is positioned near the second end of the trench and includes integrated photodetectors.

19 Claims, 4 Drawing Sheets

(56) References Cited

U.S. PATENT DOCUMENTS

| | | |
|---|---|---|
| 2012/0170265 A1 | 7/2012 | Kurt |
| 2013/0125955 A1 | 5/2013 | Hazeghi |
| 2013/0155390 A1 | 6/2013 | Jensen |
| 2013/0161730 A1 | 6/2013 | Pan |
| 2013/0280908 A1 | 10/2013 | Li |
| 2014/0001432 A1 | 1/2014 | Hall |
| 2014/0045209 A1* | 2/2014 | Chou ................. G01N 21/6452 435/34 |
| 2014/0363912 A1 | 12/2014 | Ohlsson |
| 2015/0053261 A1 | 2/2015 | Tsuchiya |
| 2015/0253321 A1* | 9/2015 | Chou ............... G01N 33/54366 435/5 |
| 2016/0144406 A1* | 5/2016 | Astier .................... B07B 13/04 209/675 |
| 2016/0146778 A1* | 5/2016 | Astier ................ G01N 15/1031 506/12 |
| 2016/0148959 A1 | 5/2016 | Cheng |

* cited by examiner

NANO-PILLAR-BASED BIOSENSING DEVICE

FIELD OF THE DISCLOSURE

The present disclosure relates generally to medical diagnostics and relates more specifically to nano-pillar-based biosensing devices.

BACKGROUND OF THE DISCLOSURE

The detection and/or monitoring of serious health conditions often involves performing diagnostics on blood, sweat, or other fluids. For instance, once a person has been diagnosed with diabetes, he will typically need to continuously monitor his blood glucose levels in order to facilitate insulin intake. In other cases, cancer survivors may need to monitor their blood for particular biomarkers (e.g., protein molecules) including receptors or antigens that can indicate a recurrence of the disease. In addition, blood tests such as enzyme-linked immunosorbent assay (ELISA) and reverse transcriptase polymerase chain reaction (PCR) can quickly identify certain types of infectious diseases.

SUMMARY OF THE DISCLOSURE

In one example, a device includes a trench formed in a substrate. The trench includes a first end and a second end that are non-collinear. A first plurality of semiconductor pillars is positioned near the first end of the trench and includes integrated light sources. A second plurality of semiconductor pillars is positioned near the second end of the trench and includes integrated photodetectors.

In another example, a device includes a trench formed in a substrate. The trench has an angular shape including at least one bend. A first plurality of semiconductor pillars is positioned near a first end of the trench and includes integrated light sources. A second plurality of semiconductor pillars is positioned near a second end of the trench and includes integrated photodetectors. A light blocker positioned inside the bend.

In another example, a method includes treating a fluid sample with a fluorophore that binds to particles in the fluid sample. The sample is then passed through a trench including a plurality of microfluidic channels, wherein a first end of the trench includes a first plurality of pillars having integrated light sources. Contact between the particles and at least one of the light sources causes the fluorophore to emit light. Trajectories of the particles are tracked through the plurality of microfluidic channels by detecting the light, using a photodetector integrated into one of a second plurality of pillars positioned near a second end of the trench.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the Figures.

DETAILED DESCRIPTION

In one example, a nano-pillar-based biosensing device is disclosed. As discussed above, the detection and/or monitoring of serious health conditions often involves performing diagnostics on blood, sweat, or other fluids. In many cases, the demand has grown for small, lightweight devices that can perform these diagnostics, including portable or wearable devices. For instance, continuous monitoring of blood glucose levels has been facilitated by the availability of portable glucose meters. However, the diagnoses of many other health conditions require that a sample of blood or other fluid, once obtained, be transported to a laboratory or other remote facility for analysis (e.g., with discrete optical imaging systems, microscopes, or other device). This can delay diagnoses of time-critical conditions and also compromise the integrity of the sample, leading to inaccurate results.

Examples of the present disclosure provide a portable system-on-chip (SoC) that integrates microfluidic channels with light sources, detectors, and complementary metal-oxide-semiconductor (CMOS) circuitry. By integrating light sources or photodetectors into nano-pillars that are also capable of sorting proteins (e.g., based on size), a compact device can be fabricated for performing biosensing applications. The device can be fabricated as a standalone device that performs collection, processing, and diagnostics on a fluid sample, or the device can communicate with a remote portable device (e.g., a smart phone or tablet computer) that includes software for performing diagnostics.

Figure 1:
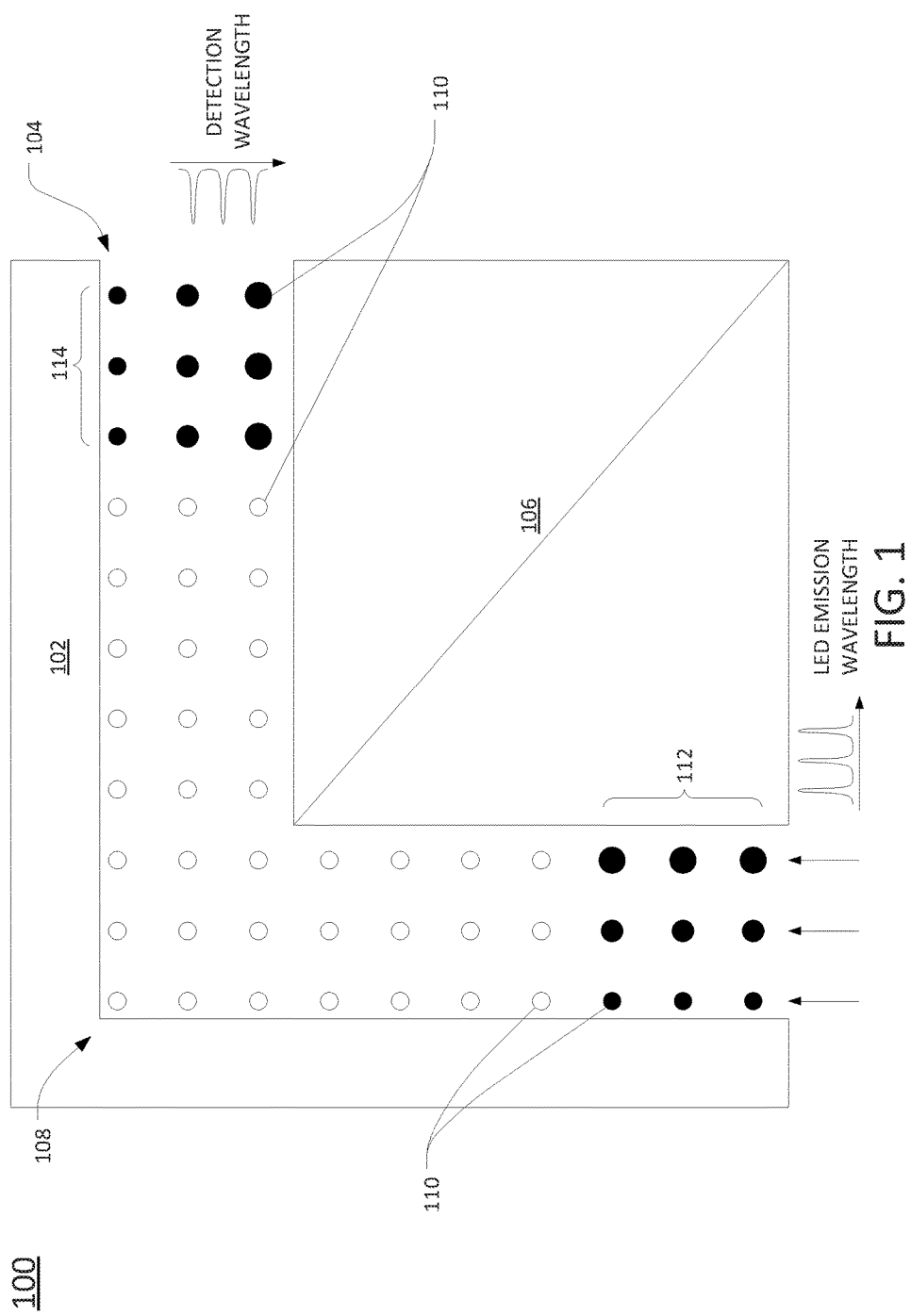
FIG. 1 illustrates a top view of an example biosensing device of the present disclosure.

FIG. 1 illustrates a top view of an example biosensing device 100 of the present disclosure. As illustrated, the device 100 generally comprises a substrate 102, a trench 104 formed in the substrate 102, and a light blocker 106 positioned on the substrate 102, adjacent to the trench 104.

The substrate 102 may comprise, for example, a silicon substrate. The trench 104 comprises a recess in the substrate 102, i.e., an area in which a portion of the substrate material is removed to form a passage. In one example, the trench 104 has an angular shape, e.g., such that the ends of the trench are not collinear. For instance, the trench 104 may form a right angle, as illustrated in FIG. 1. However, in other examples, the angle formed by the trench may be smaller or greater than ninety degrees. In further examples still, the trench 104 may have a curved shaped. In each instance, however, the trench 104 includes at least one bend or corner 108 at which the passage formed by the trench 104 changes direction. In one example, the light blocker 106 is positioned inside of the corner 108. The light blocker may comprise, for instance, a layer of metal.

A plurality of nano-pillars 110 is positioned inside the trench 104. In one example, the nano-pillars 110 comprise silicon-based, nano-scale pillars that extend upward from the recessed surface of the substrate 102. The sizing and spacing of the nano-pillars 110 creates a plurality of microfluidic channels through which a sample fluid (e.g., blood or other fluid) can flow from one end of the trench 104 to the other end. In addition, the sizing of and spacing between the nano-pillars 110 can be optimized to sort proteins in the sample fluid, e.g., such that proteins of certain sizes are forced along particular channels of the plurality of microfluidic channels.

In one example, subsets of the nano-pillars 110 are functionalized. That is, the subsets include nano-pillars that have been configured to provide functions in addition to sorting. For instance, the device 100 illustrated in FIG. 1 includes two functionalized subsets of nano-pillars 110. A first subset 112 positioned near a first end of the trench 104 comprises nano-pillars 110 that include integrated light sources, such as integrated light emitting diodes (LEDs). The specific wavelength or wavelengths that can be emitted by a given nano-pillar 110 may be tuned in one example by adjusting the size of the pillar (e.g., diameter) and/or the material from which the pillar is fabricated to enable excitation of one or more particular fluorophores. For instance, a nano-pillar 110 integrating an indium gallium nitride-based light source may emit light in the 300-400 nanometer wavelength range; a nano-pillar 110 integrating a gallium arsenide-based or aluminum gallium arsenide-based light source may emit light in the 700-850 nanometer wavelength range; and a nano-pillar 110 integrating an indium gallium arsenic phosphide-based light source may emit light in the 1310-1550 nanometer wavelength range. Thus, the configurations of the nano-pillars 110 in the first subset 112 need not be identical, but may include nano-pillars 110 of varying sizes, materials, and configurations. In one example, each nano-pillar 110 in the first subset 112 is individually addressable (e.g., by an active matrix or passive matrix circuits) to emit light. One specific example of a nano-pillar including an integrated light source is discussed in further detail in connection with FIG. 3.

A second subset 114 positioned near a second end of the trench 104 comprises nano-pillars 110 that include integrated photodetectors that are tuned to detect light of specific wavelengths. The specific wavelength or wavelengths that can be detected by a given nano-pillar 110 may be tuned in one example by adjusting the size of the pillar (e.g., diameter) and/or the material from which the pillar is fabricated. For instance, a nano-pillar 110 integrating an indium gallium nitride-based photodetector may detect light in the 300-400 nanometer wavelength range; a nano-pillar 110 integrating a silicon-based photodetector may detect light in the 400-850 nanometer wavelength range; a nano-pillar 110 integrating a gallium arsenide-based photodetector may detect light in the 500-850 nanometer wavelength range; and a nano-pillar 110 integrating an indium gallium arsenide-based photodetector may detect light in the 850-1550 nanometer wavelength range. Thus, the configurations of the nano-pillars 110 in the second subset 114 need not be identical, but may include nano-pillars 110 of varying sizes, materials, and configurations. Some specific examples of nano-pillars including integrated photodetector functionality are discussed in further detail in connection with FIGS. 4A-4C.

In this case, the light blocker 106 is positioned to minimize detection by the second subset 114 of light emitted by the first subset 112. The shape of the trench 104 also helps in this respect. As discussed in further detail below, the first and second subsets 112 and 114 of nano-pillars 110 allow the device 100 to track particles in a sample fluid, which, in turn, may aid in the detection and diagnosis of certain medical conditions.

In some examples, the biosensing system 100 can be fabricated as a disposable, one-time-use chip. In this case, a separate reader device may be fabricated to analyze data collected by the biosensing system 100.

Figure 2:
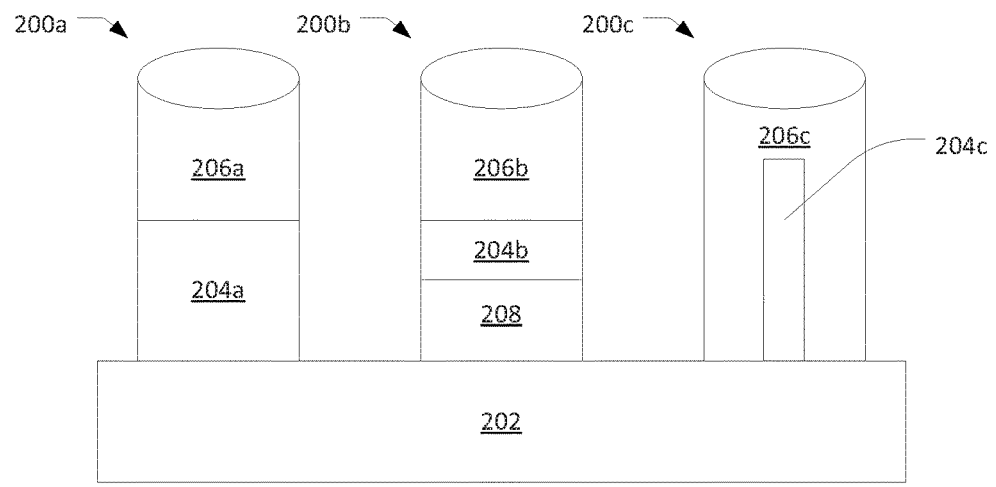
FIG. 2 illustrates cross sectional views of three general examples of functionalized nano-pillars that may be used in the biosensing device of FIG. 1.

FIG. 2 illustrates cross sectional views of three general examples of functionalized nano-pillars 200a-200c that may be used in the biosensing device 100 of FIG. 1. Thus, any of the nano-pillars 200a-200c may be used as the basis for a nano-pillar with integrated light source or a nano-pillar with an integrated photodetector, e.g., as illustrated in the first subset 112 and second subset 114 of the nano-pillars 110.

In general, each of the nano-pillars 200a-200c is fabricated as a p-i-n diode on a semiconductor substrate 202. In one example, the semiconductor substrate 202 may be n-doped.

In a first example, the nano-pillar 200a comprises an undoped, intrinsic layer 204a fabricated directly on the n-doped substrate 202. A p-doped layer 206a is then fabricated directly on the intrinsic layer 204a.

In a second example, the nano-pillar 200b comprises an n-doped layer 208 fabricated directly on the n-doped substrate. An undoped, intrinsic layer 204b is fabricated directly on the n-doped layer 208. A p-doped layer 206b is then fabricated directly on the intrinsic layer 204b.

In a third example, the nano-pillar 200c comprises a pillar of p-doped material 206c fabricated directly on the n-doped substrate 202. The pillar of p-doped material 206c includes an undoped, intrinsic core 204c.

The configurations illustrated in FIG. 2 may be used to fabricate nano-pillars having integrated light sources (e.g., such as the nano-pillars 110 in the first subset 112 of FIG. 1) or nano-pillars having integrated photodetectors (e.g., such as the nano-pillars 110 in the second subset 114 of FIG. 1). Where the nano-pillars include integrated light sources, a light source such as an LED light source may be fabricated in the intrinsic layer of the p-i-n diode. Where the nano-pillars include integrated photodetectors, the p-i-n diode may form the photodiode, as described in further detail with respect to FIGS. 4A-4C.

Figure 3:
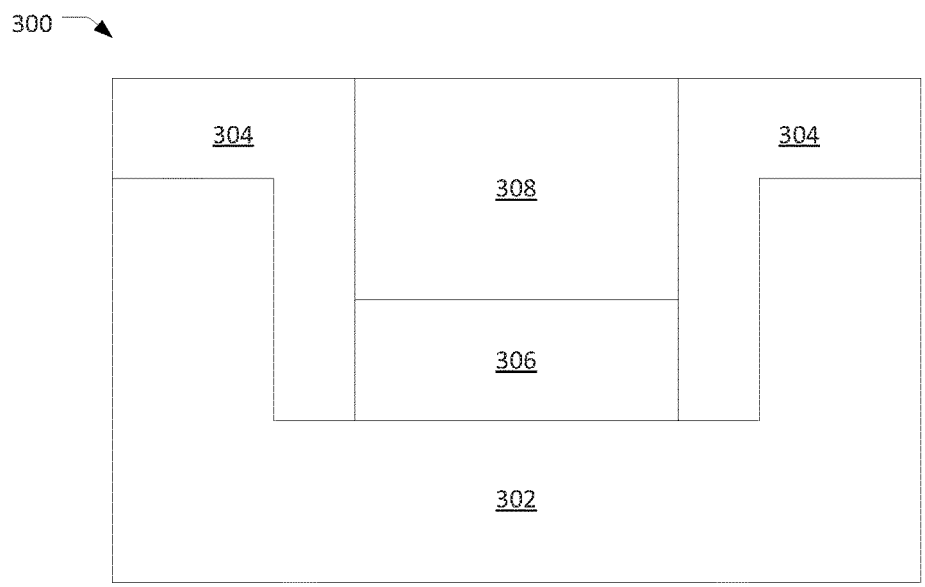
FIG. 3 illustrates a cross sectional view of one example of a nano-pillar that has been configured to emit light.

FIG. 3 illustrates a cross sectional view of one example of a nano-pillar 300 that has been configured to emit light. Thus, the nano-pillar 300 may be used, for instance, in the first subset 112 of nano-pillars 110 illustrated in FIG. 1.

As illustrated, the nano-pillar 300 is fabricated on a semiconductor substrate 302 such as a silicon substrate. The substrate 302 may be patterned with a series of trenches. The sidewalls of the trenches may be lined with a layer 304 of insulating material, such as silicon dixode. A layer 306 of a semiconductor material, such as germanium, may line the bottoms of the trenches. A light emitting diode 308, such as an LED formed from one or more Group III-V materials, is grown on the layer 306 of semiconductor material.

Figure 4:
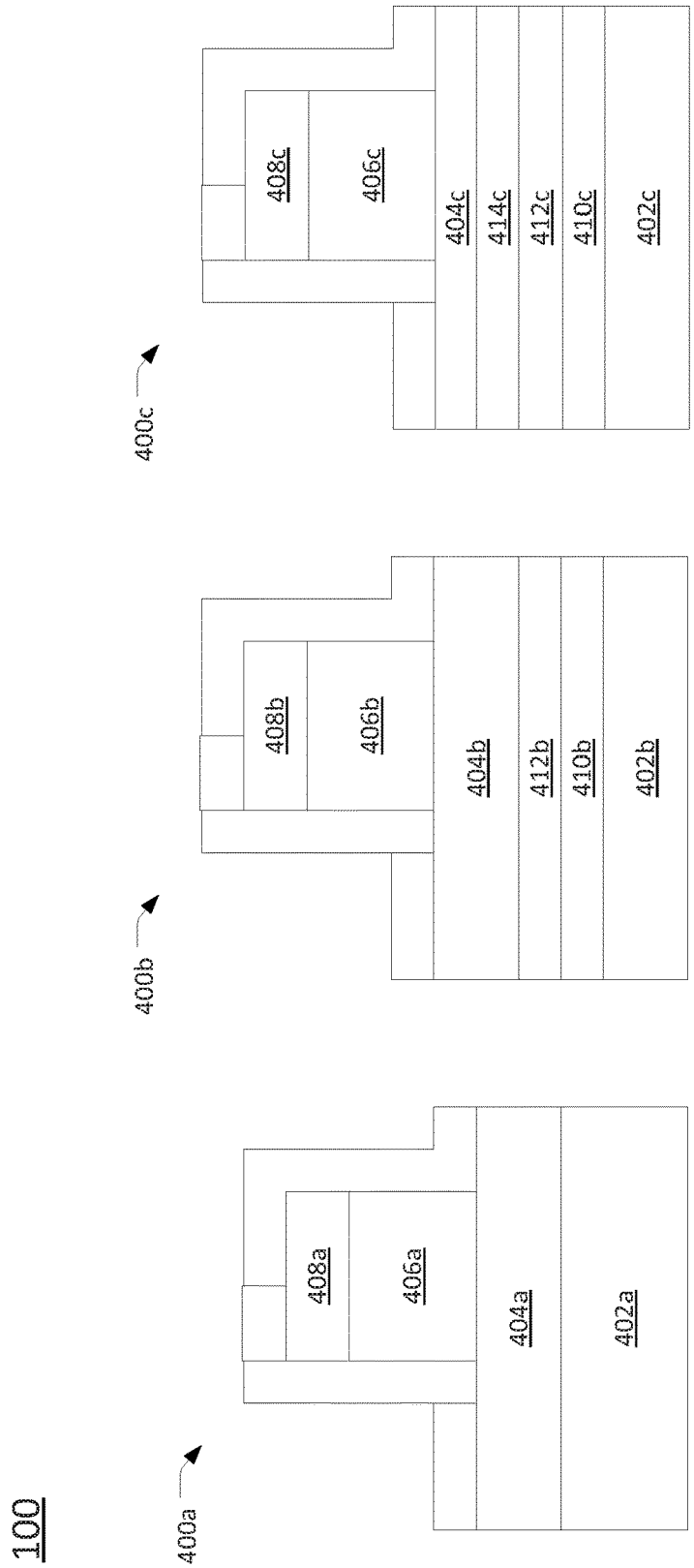
FIGS. 4A-4C illustrate a cross sectional views of three examples of a nano-pillar that have been configured to operate as detectors.

FIGS. 4A-4C illustrate cross sectional views of three examples of nano-pillar 400a-400c that have been configured to operate as photodetectors. Thus, the nano-pillar 400a, 400b, or 400c may be used, for instance, in the second subset 114 of nano-pillars 110 illustrated in FIG. 1. In each example, the nano-pillar 400a, 400b, or 400c is fabricated as a p-i-n photodetector on a semiconductor substrate. However, in other examples, the photodetectors may be fabricated as p-n diodes, without an intervening intrinsic layer.

Referring to FIG. 4A, the example nano-pillar 400a is fabricated on a semiconductor substrate 402a, such as a gallium arsenide substrate. The substrate 402a may have a thickness of approximately 850 nanometers. A first contact 404a, formed, for example, from an n-type semiconductor material such as n+ gallium arsenide is fabricated on the substrate 402a. An absorber layer 406a, formed, for example, from undoped, intrinsic gallium arsenide, is then fabricated on the first contact 404a. A second contact 408a, formed, for example, from p+ gallium arsenide, is then fabricated on absorber layer 406a. Thus, the first contact 404a, absorber layer 406a, and second contact 408a collectively form a gallium arsenide p-i-n diode on a gallium arsenide substrate 402a.

Referring to FIG. 4B, the example nano-pillar 400b is fabricated on a semiconductor substrate 402a, such as a silicon substrate. The substrate 402b may have a thickness of approximately 850 nanometers. A first buffer layer 410b, formed, for example, from germanium, is fabricated on the substrate 402b. A second buffer layer 412b, formed, for example, from indium gallium phosphide, is fabricated on the first buffer layer 410b. A first contact 404b, formed, for example, from an n-type semiconductor material such as n+ gallium arsenide is fabricated on the second buffer layer 412b. An absorber layer 406b, formed, for example, from undoped, intrinsic gallium arsenide, is then fabricated on the first contact 404b. A second contact 408b, formed, for example, from p+gallium arsenide, is then fabricated on absorber layer 406b. Thus, the first contact 404b, absorber layer 406b, and second contact 408b collectively form a gallium arsenide p-i-n diode on a silicon substrate 402b (with a multi-layer buffer formed between the p-i-n diode and the substrate).

Referring to FIG. 4C, the example nano-pillar 400c is fabricated on a semiconductor substrate 402c, such as a silicon substrate. The substrate 402c may have a thickness between approximately 1310 and 1550 nanometers. A first buffer layer 410c, formed, for example, from germanium, is fabricated on the substrate 402c. A second buffer layer 412c, formed, for example, from gallium arsenide, is fabricated on the first buffer layer 410c. A third buffer layer 414c, formed, for example, from indium phosphide, is fabricated on the second buffer layer 412c. A first contact 404c, formed, for example, from an n-type semiconductor material such as n+ indium gallium arsenide is fabricated on the third buffer layer 414c. An absorber layer 406c, formed, for example, from undoped, intrinsic indium gallium arsenide, is then fabricated on the first contact 404c. A second contact 408c, formed, for example, from p+ indium gallium arsenide, is then fabricated on absorber layer 406c. Thus, the first contact 404c, absorber layer 406c, and second contact 408c collectively form an indium gallium arsenide p-i-n diode on a silicon substrate 402c (with a multi-layer buffer formed between the p-i-n diode and the substrate).

Figure 5:
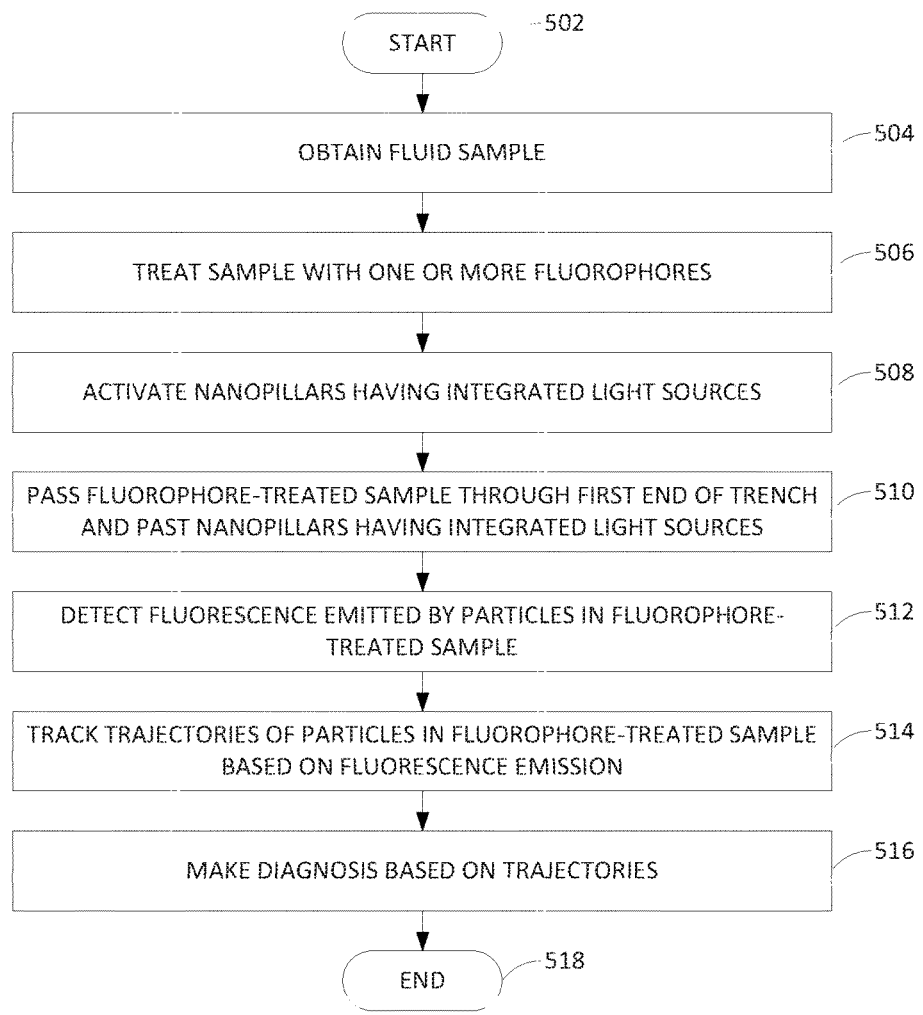
FIG. 5 is a flow diagram illustrating one example of a method for processing a sample.

FIG. 5 is a flow diagram illustrating one example of a method 500 for processing a sample. The method 500 may be performed, for instance, using the biosensing device 100 illustrated in FIG. 1. As such, reference is made in the discussion of the method 500 to various elements of FIG. 1. However, it will be appreciated that the method 500 could be performed using a device with a configuration that differs from the configuration shown in FIG. 1.

The method 500 begins in step 502. In step 504, a sample is obtained. In one example, the sample is a fluid sample, such as blood or another fluid. The sample is to be analyzed for evidence of one or more medical conditions.

In step 506, the sample is treated with one or more fluorophores (i.e., fluorescent chemical compounds that emit light upon excitation). Different fluorophores will bind to different particles that may or may not be present in the sample.

In step 508, the first subset 112 of nano-pillars 110 is activated. For instance, the nano-pillars 110 including integrated light sources may be activated to emit light of one or more wavelengths.

In step 510, the fluorophore-treated sample is passed through the first end of the trench 104 in the biosensing device 100, such that the sample comes into contact with the first subset 112 of nano-pillars 110. As the particles in the sample hit the nano-pillars 110 in the first subset 112, the fluorophores that have bound to the particles will become excited and cause the particles to emit fluorescence. The emitted fluorescence will exhibit signatures that are unique to the fluorophores.

In step 512, the second subset 114 of nano-pillars 110 detects the fluorescence emitted by the fluorophore-bound particles. In one example, the position of the light blocker 106 ensures that the light detected by the second subset 114 of nano-pillars 110 is the fluorescence emitted by the particles of the sample rather than the light emitted by the light sources of the first subset 112 of nano-pillars 110.

In step 514, the second subset 114 of nano-pillars 110 tracks the trajectories of the particles through the trench 104, based on tracking of the emitted fluorescence. That is, because each fluorophore is selected to bind to a specific particle and emits a unique signature fluorescence when excited, the trajectory taken by the specific particle can be tracked by detecting and following the emission of the signature fluorescence.

In step 516, a diagnosis is made based on the tracking of particle trajectories. In particular, particles of different sizes will have different trajectories (e.g., based on the sizing and spacing of the nano-pillars 110, which will force particles of certain sizes along particular microfluidic channels). Thus, based on the trajectory, the particle size can be estimated. Then, based on the particle size, a medical diagnosis may be made (e.g., based on the presence or absence of particles of a certain size). The diagnosis may indicate that no medical conditions of concern are present, or the diagnosis may indicate the potential presence of a condition that requires medical attention.

The method 500 ends in step 518.

Although various embodiments which incorporate the teachings of the present invention have been shown and described in detail herein, those skilled in the art can readily devise many other varied embodiments that still incorporate these teachings.

What is claimed is:
1. A method comprising:
   treating a fluid sample with a fluorophore that binds to particles in the fluid sample;
   passing the sample through a trench, wherein a first end of the trench includes a first plurality of pillars having integrated light sources and a plurality of microfluidic channels that pass between the first plurality of pillars, and wherein contact between the particles and at least one of the light sources causes the fluorophore to emit light; and
   tracking trajectories of the particles through the plurality of microfluidic channels by detecting the light, using a photodetector integrated into one of a second plurality of pillars positioned near a second end of the trench, wherein the plurality of microfluidic channels also passes between the second plurality of pillars.
2. The method of claim 1, further comprising:
   blocking light emitted by the integrated light sources from reaching the photodetector.
3. The method of claim 1, wherein the first end of the trench and the second end of the trench are non-collinear.
4. The method of claim 1, wherein the trench has an angular shape including at least one bend.

5. The method of claim 1, further comprising:
sorting the particles from other particles having different sizes, using a third plurality of pillars positioned between the first plurality of pillars and the second plurality of pillars, wherein the plurality of microfluidic channels also passes between the third plurality of pillars.

6. The method of claim 1, wherein the first plurality of pillars includes pillars of at least two different sizes.

7. The method of claim 1, wherein the integrated light sources include light sources configured to emit light in at least two different wavelength ranges.

8. The method of claim 1, wherein the second plurality of pillars includes pillars of at least two different sizes.

9. The method of claim 1, wherein the second plurality of pillars includes a first pillar including a first integrated photodetector and a second pillar including a second integrated photodetector, wherein the first integrated photodetector is configured to detect light in a first wavelength range, and wherein the second integrated photodetector is configured to detect light in a second wavelength range that is different from the first wavelength range.

10. The method of claim 1, further comprising:
estimating sizes of the particles based on the trajectories; and
diagnosing a medical condition based on at least some of the particles being estimated to be of a defined size.

11. The method of claim 10, wherein the sizes of the particles are estimated from the trajectories based on known sizings and spacings of those of the plurality of microfluidic channels through which the particles pass.

12. The method of claim 10, wherein the estimating and the diagnosing are performed locally on a chip containing the trench, the plurality of microfluidic channels, the first plurality of pillars, and the second plurality of pillars.

13. The method of claim 10, wherein the estimating and the diagnosing are performed by a device that is remote from a chip containing the trench, the plurality of microfluidic channels, the first plurality of pillars, and the second plurality of pillars.

14. The method of claim 1, further comprising:
estimating sizes of the particles based on the trajectories; and
diagnosing a medical condition based on none of the particles being estimated to be of a defined size.

15. The method of claim 14, wherein the sizes of the particles are estimated from the trajectories based on known sizings and spacings of those of the plurality of microfluidic channels through which the particles pass.

16. The method of claim 14, wherein the estimating and the diagnosing are performed locally on a chip containing the trench, the plurality of microfluidic channels, the first plurality of pillars, and the second plurality of pillars.

17. The method of claim 14, wherein the estimating and the diagnosing are performed by a device that is remote from a chip containing the trench, the plurality of microfluidic channels, the first plurality of pillars, and the second plurality of pillars.

18. The method of claim 1, wherein the trench, the plurality of microfluidic channels, the first plurality of pillars, and the second plurality of pillars are contained on a portable system-on-chip.

19. The method of claim 1, wherein the treating comprises treating the fluid sample with a plurality of different fluorophores, wherein each fluorophore of the plurality of different fluorophores binds to particles of a different type in the fluid sample.

* * * * *